United States Patent [19]

Sandler

[11] Patent Number: 4,987,249
[45] Date of Patent: Jan. 22, 1991

[54] 2,4-PENTANEDIONE-1,5-DISULFONIC ACID AND METHOD FOR PREPARING THE SAME

[75] Inventor: Stanley R. Sandler, Springfield, Pa.

[73] Assignee: Atochem North America, Inc., Philadelphia, Pa.

[21] Appl. No.: 413,793

[22] Filed: Sep. 28, 1989

[51] Int. Cl.$^5$ .......................................... C07C 303/00
[52] U.S. Cl. .................................................. 562/102
[58] Field of Search .............................. 562/109, 102

[56] References Cited

U.S. PATENT DOCUMENTS

| | | | |
|---|---|---|---|
| 2,195,088 | 3/1940 | Keppler | 562/109 |
| 2,308,841 | 1/1943 | Werntz | 562/109 |

FOREIGN PATENT DOCUMENTS 0289952  11/1988  European Pat. Off. ............ 562/102

*Primary Examiner*—Alan Siegel
*Attorney, Agent, or Firm*—Panitch Schwarze, Jacobs & Nadel

[57] ABSTRACT

2,4-pentanedione-1,5-disulfonic acid is prepared by reacting chlorosulfonic acid with 2,4-pentanedione with heating to a temperature greater than about 50° C., preferably in the presence of an anhydrous solvent. The method of this invention generally yields 2,4-pentanedione-1,5-disulfonic acid in excess of about 60 percent. The novel pentanedionedisulfonic acid (2,4-pentanedione-1,5-disulfonic acid acetylacetone disulfonic acid) is disclosed.

2 Claims, No Drawings

2,4-PENTANEDIONE-1,5-DISULFONIC ACID AND METHOD FOR PREPARING THE SAME

CROSS REFERENCE TO RELATED APPLICATION

The present application is related to my copending U.S. Pat. application for "2,4-Pentanedionemonosulfonic Acid and Method for Preparing the Same," Ser. No. 413,575, filed concurrently herewith.

FIELD OF THE INVENTION

The present invention is directed to 2,4-pentanedione-1,5-disulfonic acid (acetylacetone disulfonic acid) and methods for preparing the same.

BACKGROUND OF THE INVENTION

To the best of the inventor's belief, the literature is devoid of any information regarding 2,4-pentanedione-1,5-disulfonic acid.

Copending Patent Application Ser. No. 044,933, filed May 1, 1987, discloses the preparation of propanone-1,3-disulfonic acid (acetone disulfonic acid) by reacting chlorosulfonic acid with acetone (2-propanone). The disclosure of U.S. Pat. Application Ser. No. 044,933 is incorporated herein by reference. As disclosed therein, the reaction of acetone with chlorosulfonic acid results in a diacid substitution at the first and third carbons.

Keto-substituted alkane sulfonic acids are useful as: (1) an esterification catalyst; (2) an alkylation catalyst; (3) a chelating agent; and (4) a starting material to give polymeric ionexchange resins, among others. Such sulfonic acids are also useful in undergoing condensation reactions with other aldehydes and ketones because of their activated methylene groups. These reactions may lead to monomeric or polymeric compositions also having the uses described above. The very reactive methylene groups also allow these compounds to enolyze, thereby making them very useful in various substitution reactions involving electrophilic reagents.

SUMMARY OF THE INVENTION

The present invention is directed to the novel pentanedionedisulfonic acid, 2,4-pentanedione-1,5-disulfonic acid (2,4-pentanedionedisulfonic acid or acetylacetone disulfonic acid). In addition, the present invention is directed to a method of preparing 2,4-pentanedione-1,5-disulfonic acid comprising reacting 2,4-pentanedione (acetylacetone) with chlorosulfonic acid at a temperature greater than about 50° C. The reaction is preferably carried out in the presence of a higher boiling, anhydrous solvent, such as carbon tetrachloride, and the viscous product may be separated by dissolving it in water and phase separating the aqueous acid solution from the solvent. 2,4-pentanedionesulfonic acid is produced as a by-product of the method disclosed herein.

DETAILED DESCRIPTION OF THE PREFERRED EMBODIMENTS

According to the present invention, 2,4-pentanedione-1,5-disulfonic acid is prepared by reacting chlorosulfonic acid with 2,4-pentanedione (acetylacetone) in the presence or absence of solvents at a temperature greater than about 50° C. Copending patent application Ser. No. 044,933 discloses, as stated above, the preparation of propanone-1,3-disulfonic acid by reacting chlorosulfonic acid with acetone. Substituting 2,4-pentanedione (acetylacetone) for acetone (2-propanone) in that reaction, one skilled in the art would expect a similar 1,3-diacid substitution. Especially where 3.0 or more moles of chlorosulfonic acid are reacted per mole of 2,4-pentanedione, tri- or polysulfonic acids would be expected. Surprisingly, however, the 1,5-disulfonic acid results when using 2,4-pentanedione, with no tri- or polysulfonic acid production.

In addition, because the third carbon of pentanedionesulfonic acid is the most reactive (enolyzable), one skilled in the art would expect that a disulfonic acid resulting from the reaction between 2,4-pentanedione and chlorosulfonic acid would have one sulfonic acid group at the 3 position. However, surprisingly, the disulfonic acid resulting from this reaction is 2,4-pentanedione-1,5-disulfonic acid where the sulfonic acid groups are at the 1 and 5 position.

The reaction of the method according to the present invention may be represented by the following equation:

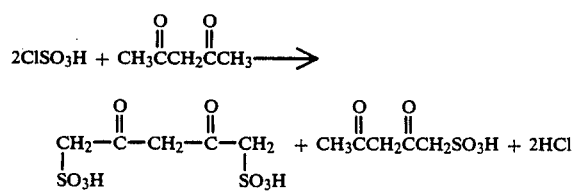

Of the two products formed, about 70% is the 1,5-disulfonic acid and 30% is the monosulfonic acid. Hydrogen chloride is formed as a by-product and is liberated during the reaction. When HCl evolution ceases, the reaction is complete.

Because chlorosulfonic acid reacts vigorously with water, it is preferred that the reactants and the reaction conditions be substantially anhydrous. For example, the primary impurities in the chlorosulfonic acid are hydrochloric and sulfuric acids, which form from contamination with water. The chlorosulfonic acid is preferably about 99–100% grade, which is available commercially from several sources. 2,4-pentanedione is also available commercially and the 100%, anhydrous grade is preferred.

The reaction of the present invention may be carried out neat or in the presence of a solvent for the reactants. The use of a solvent is preferred, although not necessary, because it allows easier separation of unreacted reactants. For example, the product phase separates readily as a viscous mass when a solvent is used. The unreacted starting materials remain dissolved in the solvent which can be separated from the product.

The solvent is preferably any inert solvent which readily dissolves the reactants and has a boiling point greater than about 50° C., preferably in the range of about 70° to about 150° C. Examples of suitable solvents include halogenated hydrocarbons, such as carbon tetrachloride (b.p. 76–77° C.), 1,1,1-trichloroethane (b.p. 74° C.) 1,1,2-trichloroethane (b.p. 113°–114° C.), 1,1,1,2-tetrachloroethane (b.p. 130°–131° C.) and 1,1,2,2-tetrachloroethane (b.p. 146–147° C.). The presently preferred solvent is carbon tetrachloride. Other suitable solvents for use in the method according to the present invention will be evident to those skilled in the art in view of this disclosure.

While the order of addition of the reactants is not particularly critical, it is presently preferred to dissolve 2,4-pentanedione in a solvent (where desired) and then add the resulting solution to chlorosulfonic acid in the reaction vessel. Such addition may be done over time. For example, 2,4-pentanedione may be added to chlorosulfonic acid over a period of about one hour. After warming the mixture to accelerate the reaction, the solvent, if present, can be refluxed while the reaction proceeds for about three to four hours.

The reaction temperature of the process must be greater than about 50° C. Below about 50° C., the yield of the 2,4-pentanedione-1,5-disulfonic acid decreases, while by-product formation of 2,4pentanedionesulfonic acid increases. Preferably, the temperature of the reaction is about of 70° C. to about 150° C., and more preferably about 70° C. to about 120° C., unless the reaction is carried out under pressure. The upper end of the temperature range is limited by the lowest boiling component of the reaction mixture. For example, when carbon tetrachloride is used as a solvent, heating up to about 76° C. to about 77° C. may be used. In any event, the temperature should not exceed about 140.5° C. (b.p. of 2,4-pentanedione; chlorosulfonic acid b.p. about 158° C.) at 1 atmosphere where no solvent having a lower boiling point is used.

The reactants are generally present with a stoichiometric excess of chlorosulfonic acid. In particular, the molar ratio of chlorosulfonic acid to 2,4-pentanedione is about 2.0:1 to 2.2:1. A ratio of about 2.05:1 presently preferred, although one skilled in the art will appreciate that higher and lower molar ratios may be used in accordance with the present invention.

Any unreacted chlorosulfonic may be recovered from the solvent, if and where desired. It is also preferred that the amount of the solvent be kept to a minimum, consistent with optimum mixing, handling and reaction conditions.

When run in a solvent medium, the 2,4-pentanedione-1,5-disulfonic acid resulting from the method of the present invention separates out as a viscous oil, which can be dissolved in water and phase separated. It is preferred to separate the solvent first to remove unreacted starting materials and thus minimize the amount of hydrochloric acid and sulfonic acid by-products formed by the hydrolysis of unreacted chlorosulfonic acid present in the aqueous product.

The product (which is typically yielded in excess of 60% using the method of the present invention) may be conveniently stored as an aqueous solution. Where desired, the disulfonic acid product may be isolated from any monosulfonic acid by-product by fractional distillation or crystallization using conventional techniques and apparatus.

The present invention will now be illustrated in more detail by reference to the following specific, non-limiting examples. In the examples, proton ($H^1$) and carbon ($C^{13}$) nuclear magnetic reaction (NMR) analyses were used to identify the 2,4-pentanedione-1,5-disulfonic acid. The solvents for the NMR analyses were deuterium oxide ($D_2O$) or deuterodimethylsulfoxide [$(CD_3)_2S=O$], with p-dioxane as the internal standard.

EXAMPLE 1

70.0 g (0.60 mole) of chlorosulfonic acid (99%) and 200 ml carbon tetrachloride were added to a 500 ml 3-necked around-bottom flask equipped with a dry-ice condenser, a thermocouple in glass tube, mechanical stirrer, nitrogen inlet, gas outlet and a dropping funnel. 30.0 g (0.3 mole) of 2,4-pentanedione (100% anhydrous) were added drop-wise at a rate so as to maintain a temperature of 48°–50° C. The solution was then heated to 75°–76° C. for 4–6hours and any carbon tetrachloride lost by evaporation was replaced. 50.0 g of water were then added and two layers separated. The top layer contained the product and weighed 119.5 g and contained 70.0% 2,4-pentanedione 1,5-disulfonic acid and 30.0% 2,4-pentanedione monosulfonic acid, as indicated by NMR analysis.

The proton nuclear magnetic resonance ($H^1$ nmr) and carbon 13 ($C^{13}$ nmr) analyses indicated the following, which were consistent with the structure of 2,4-pentanedione-1,5-disulfonic acid and 2,4-pentanedione-1-sulfonic acid.

| C Group #: |
|---|
| $$CH_3-\underset{\underset{1}{\|}}{\overset{\overset{O}{\|}}{C}}-\underset{2}{CH_2}-\underset{\underset{3}{\|}}{\overset{\overset{O}{\|}}{C}}-\underset{4}{CH_2}-\underset{5}{SO_3H} +$$ |
| $$HO_3S-\underset{6}{CH_2}-\overset{\overset{O}{\|}}{C}-\underset{7}{CH_2}-\overset{\overset{O}{\|}}{C}-\underset{8}{CH_2}-SO_3H$$ |

| $H^1$ NMR Chemical Shift (ppm) | Coupling | Proton Assignment |
|---|---|---|
| 6.64 | Singlet | $H_2O$, OH |
| 4.10 | Singlet | H6, H8 |
| 3.98 | Singlet | H3, H5 |
| 1.90 | Singlet | H1 |

| $C^{13}$ NMR Chemical Shift (ppm) | Assignment C Group # |
|---|---|
| 194.3 | C2, C7 |
| 176.6 | C4 |
| 61.8 | C3, C5, C6, C8 |
| 20.5 | C1 |

EXAMPLE 2

The procedure of Example 1 were repeated, except that the 2,4-pentanedione was dissolved in an equal amount of carbon tetrachloride before adding it to the chlorosulfonic acid dissolved in carbon tetrachloride. This method gave substantially the same results as those in Example 1 and 2,4-pentanedione-1,5-disulfonic acid was identified as the major product.

EXAMPLE 3

The procedure of Example 1 was repeated, except no carbon tetrachloride was used. At the end of the 3 to 4 hour reaction period at 75°–85° C., water was added to isolate the product as an aqueous solution. The composition of the product by NMR for this neat reaction was 42% 2,4-pentanedione-1,5-disulfonic acid and 58% 2,4-pentanedionemonosulfonic acid.

The present invention may be embodied in other specific forms without departing from the spirit or essential attributes thereof and, accordingly, reference should be made to the appended claims, rather than to the foregoing specification as indicating the scope of the invention.

I claim:
1. 2,4-pentanedione-1,5-disulfonic acid.
2. 2,4-pentanedione-1,5-disulfonic acid prepared by reacting 2,4-pentanedione with chlorosulfonic acid with heating to a temperature greater than about 50° C.

* * * * *